United States Patent [19]

Gilson

[11] 4,422,151
[45] Dec. 20, 1983

[54] LIQUID HANDLING APPARATUS

[76] Inventor: Robert E. Gilson, 4 N. Franklin Ave., Madison, Wis. 53705

[21] Appl. No.: 268,659

[22] Filed: Jun. 1, 1981

[51] Int. Cl.³ .................. G06F 15/46; G06F 15/20; G06G 7/58; G06G 7/48

[52] U.S. Cl. .................... 364/496; 364/479; 364/502; 141/130; 141/284; 104/246; 73/864.25

[58] Field of Search .............. 364/478, 479, 496, 497, 364/500, 502; 141/130, 232, 233, 284; 73/864.25, 864.24; 422/100; 198/747; 104/245, 246, 247

[56] References Cited

U.S. PATENT DOCUMENTS

| | | | |
|---|---|---|---|
| 3,623,515 | 11/1971 | Gilson | 141/130 |
| 3,625,265 | 12/1971 | Gilson | 141/284 |
| 3,687,632 | 8/1972 | Natelson | 141/130 |
| 3,753,657 | 8/1973 | Downing et al. | 141/130 |
| 4,041,763 | 8/1977 | Pflegger | 73/864.25 |
| 4,056,064 | 11/1977 | Bottomley | 104/246 |
| 4,115,861 | 9/1978 | Allington | 364/497 |
| 4,140,018 | 2/1979 | Maldatelli | 73/864.25 |
| 4,166,095 | 8/1979 | Kling et al. | 364/497 |
| 4,166,483 | 9/1979 | Norlund | 141/284 |
| 4,169,125 | 9/1979 | Rodriguez et al. | 364/497 |
| 4,199,013 | 4/1980 | Reich et al. | 141/130 |
| 4,224,278 | 9/1980 | Esch | 141/130 |
| 4,236,454 | 12/1980 | Erickson | 104/246 |
| 4,294,126 | 10/1981 | Tomoff et al. | 73/864.25 |

Primary Examiner—Jerry Smith
Assistant Examiner—William G. Niessen
Attorney, Agent, or Firm—Mason, Kolehmainen, Rathburn & Wyss

[57] ABSTRACT

A liquid handling apparatus capable of being used as a fraction collector, sampler, dispenser, diluter or the like utilizes a microprocessor and three stepping motors to move a liquid handling tube suitable for dispensing, sampling or the like in two horizontal directions and in a vertical direction with respect to an array of test tubes or similar containers. The apparatus is capable of operating in several modes of dispensing and withdrawal operations, including modes based on the number of drops dispensed or the time spent over each container. The pattern of the movement of the liquid handling tube or dispensing head is selectable to suit the mode of operation of the liquid handling apparatus as well as the type of container and the number of containers being used at a particular time.

33 Claims, 24 Drawing Figures

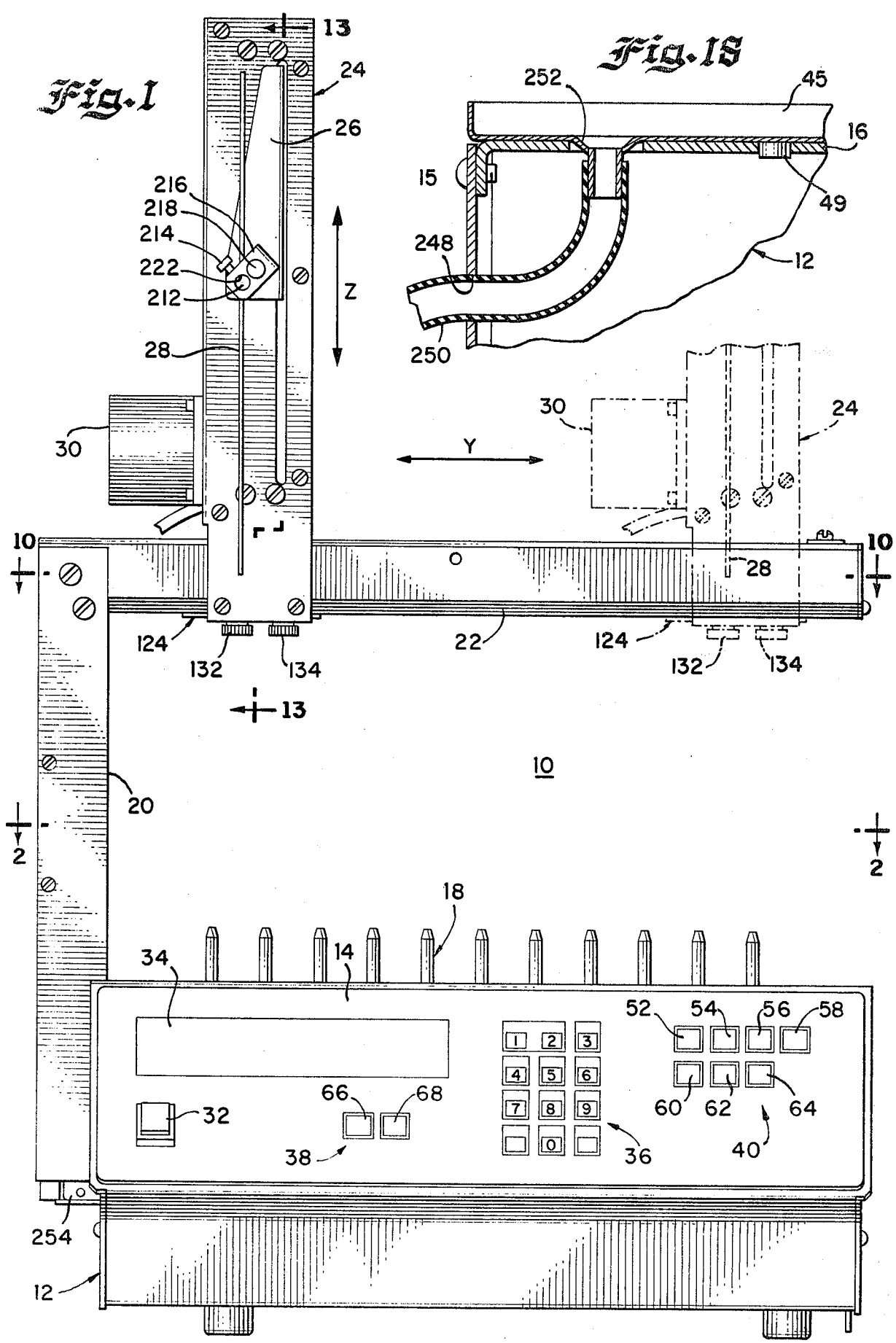

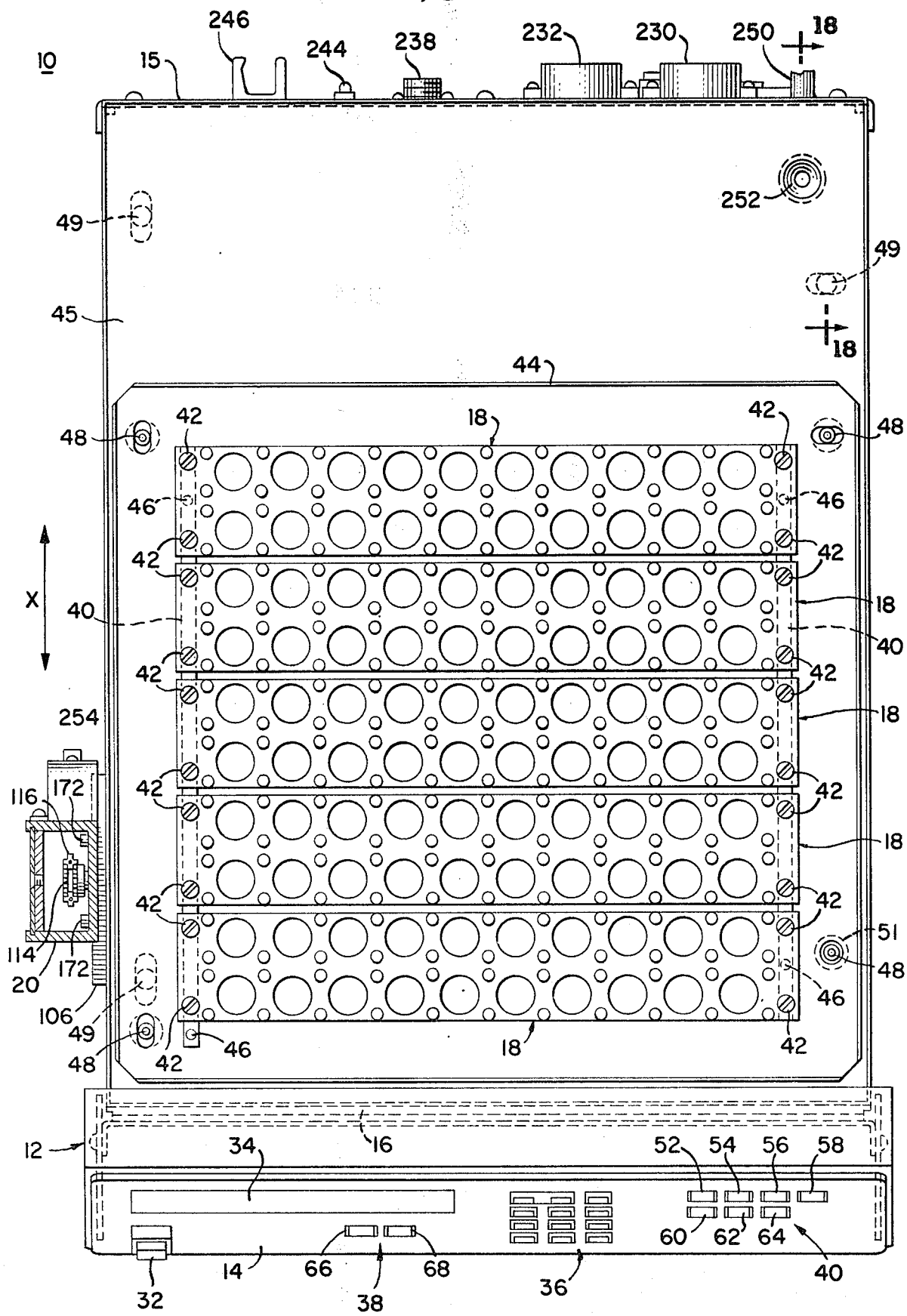

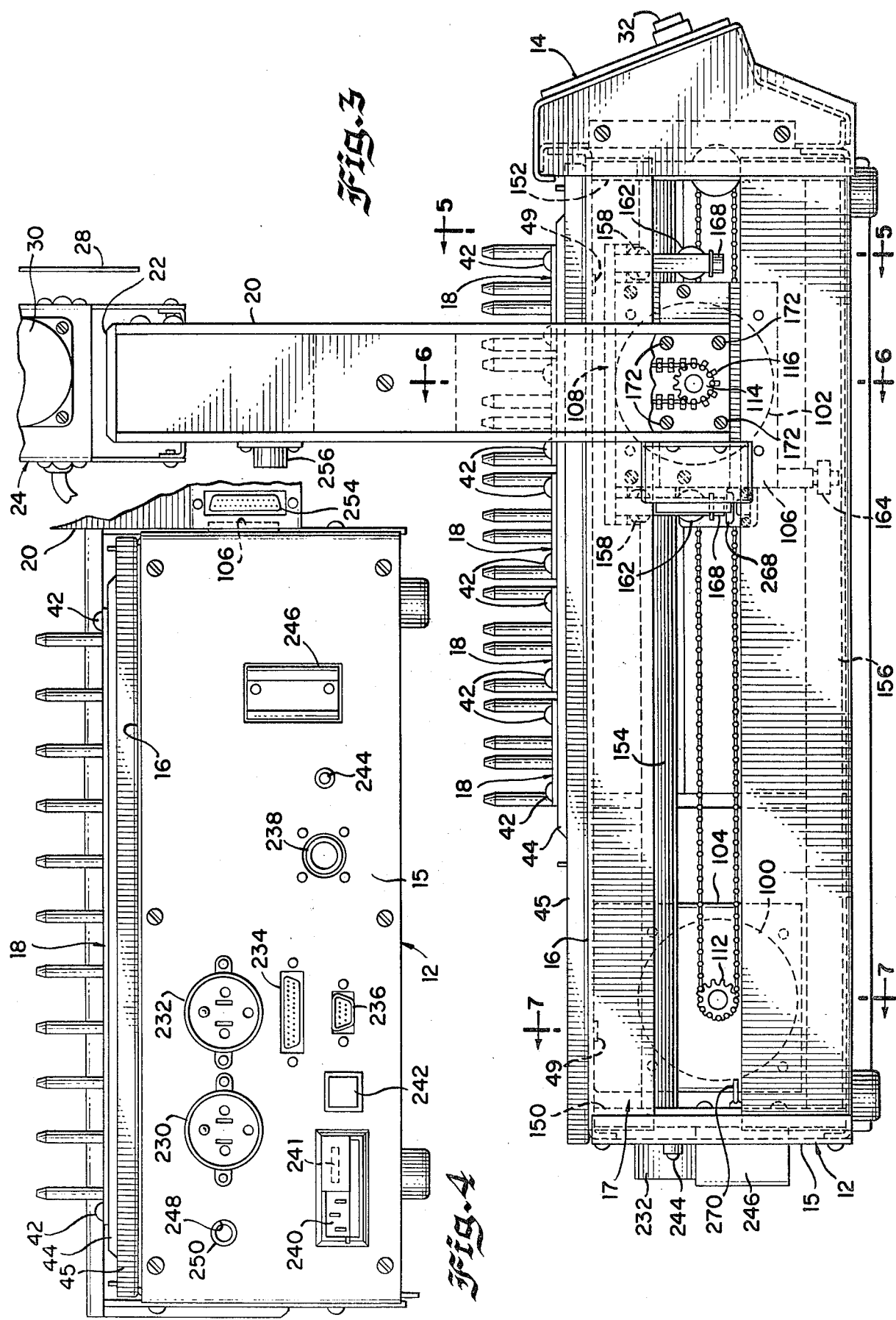

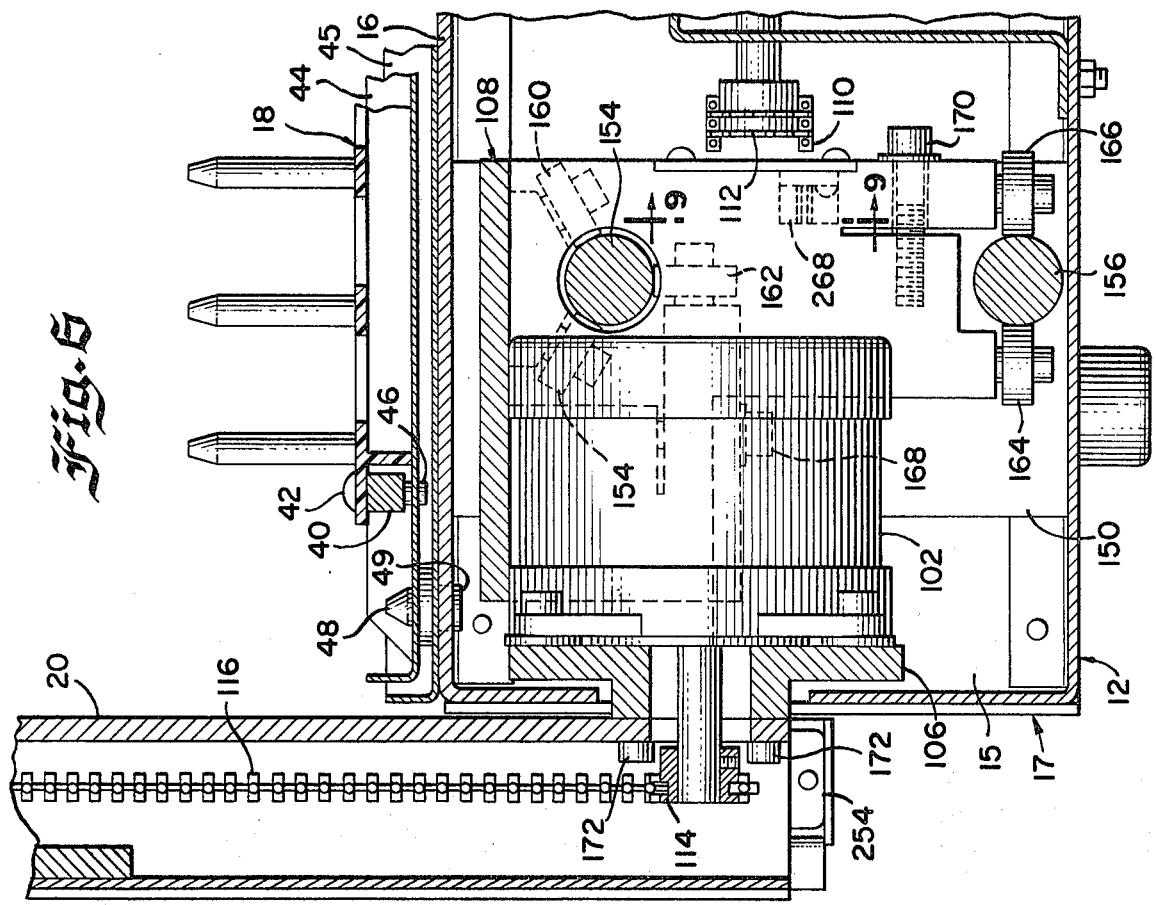
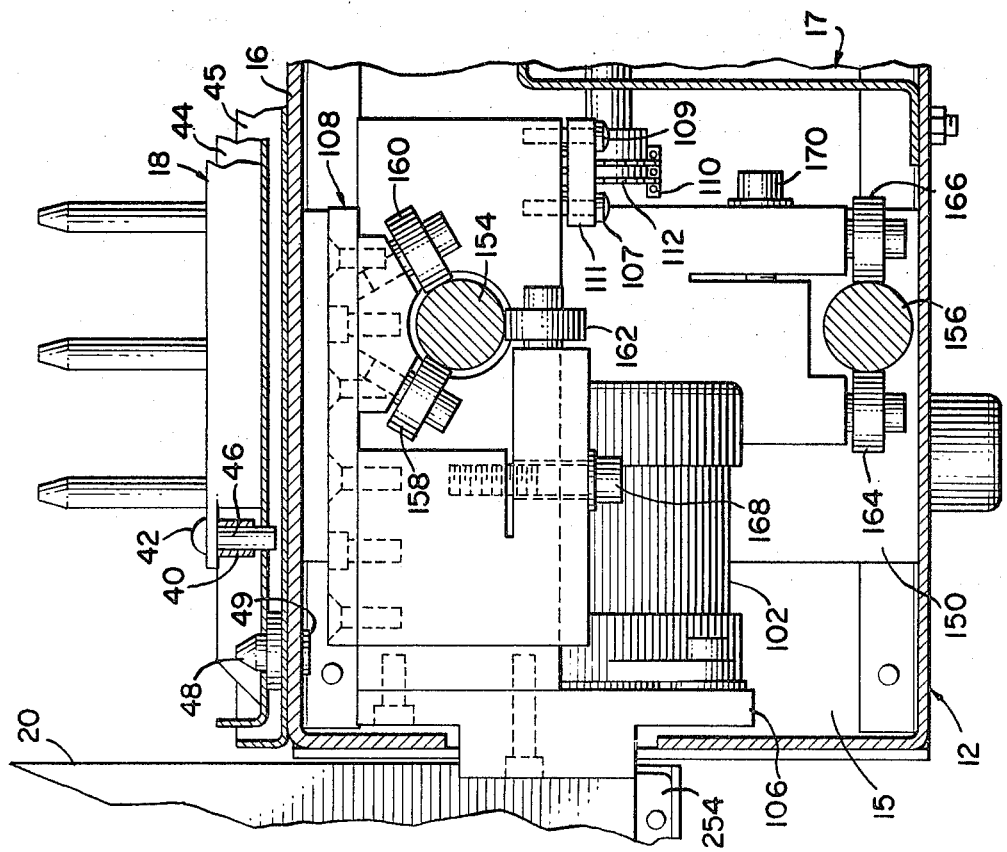

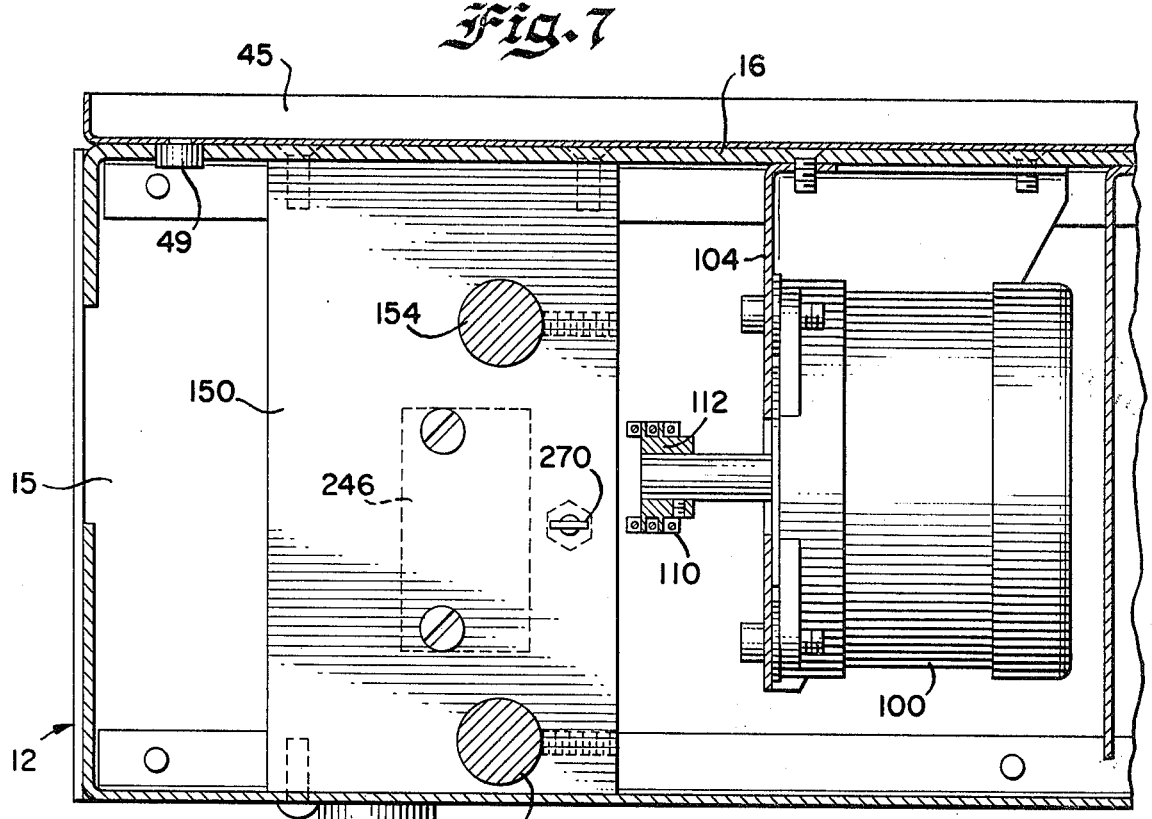
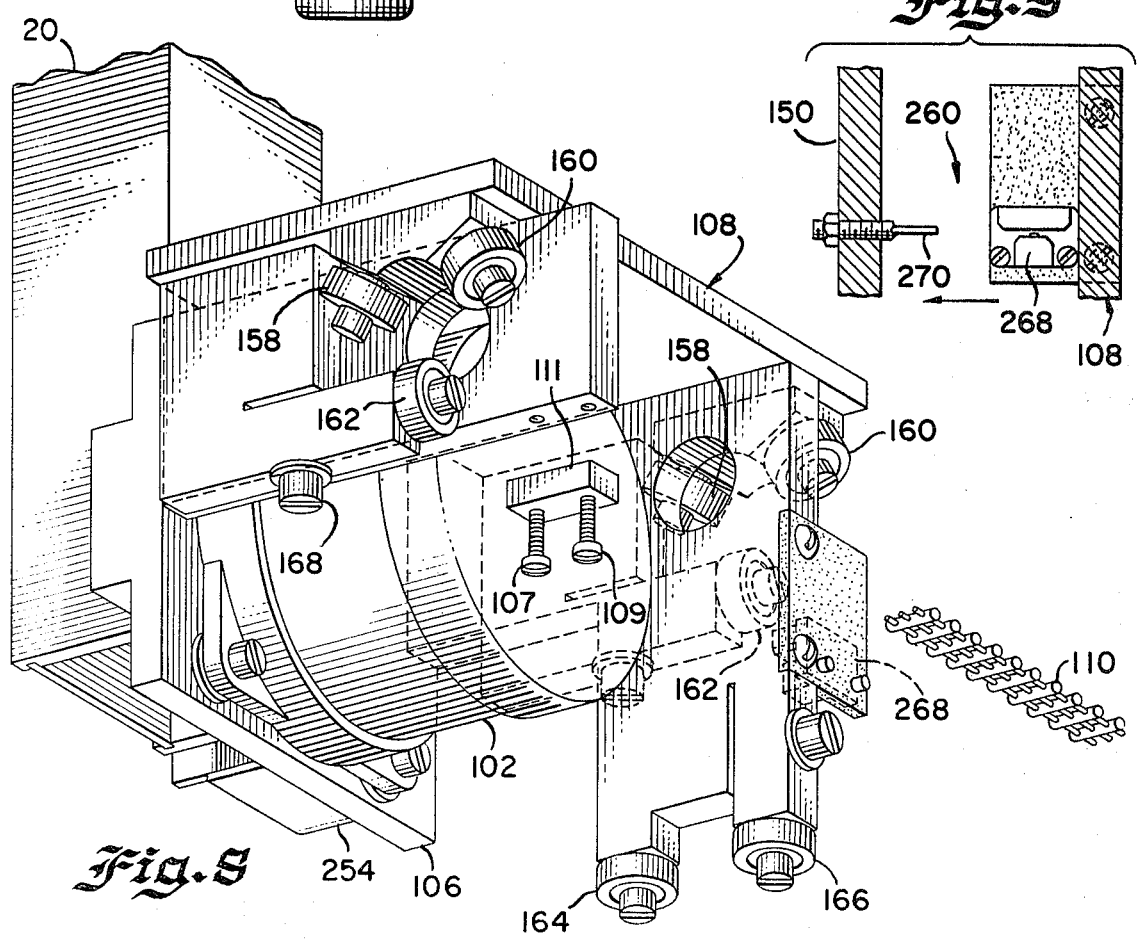

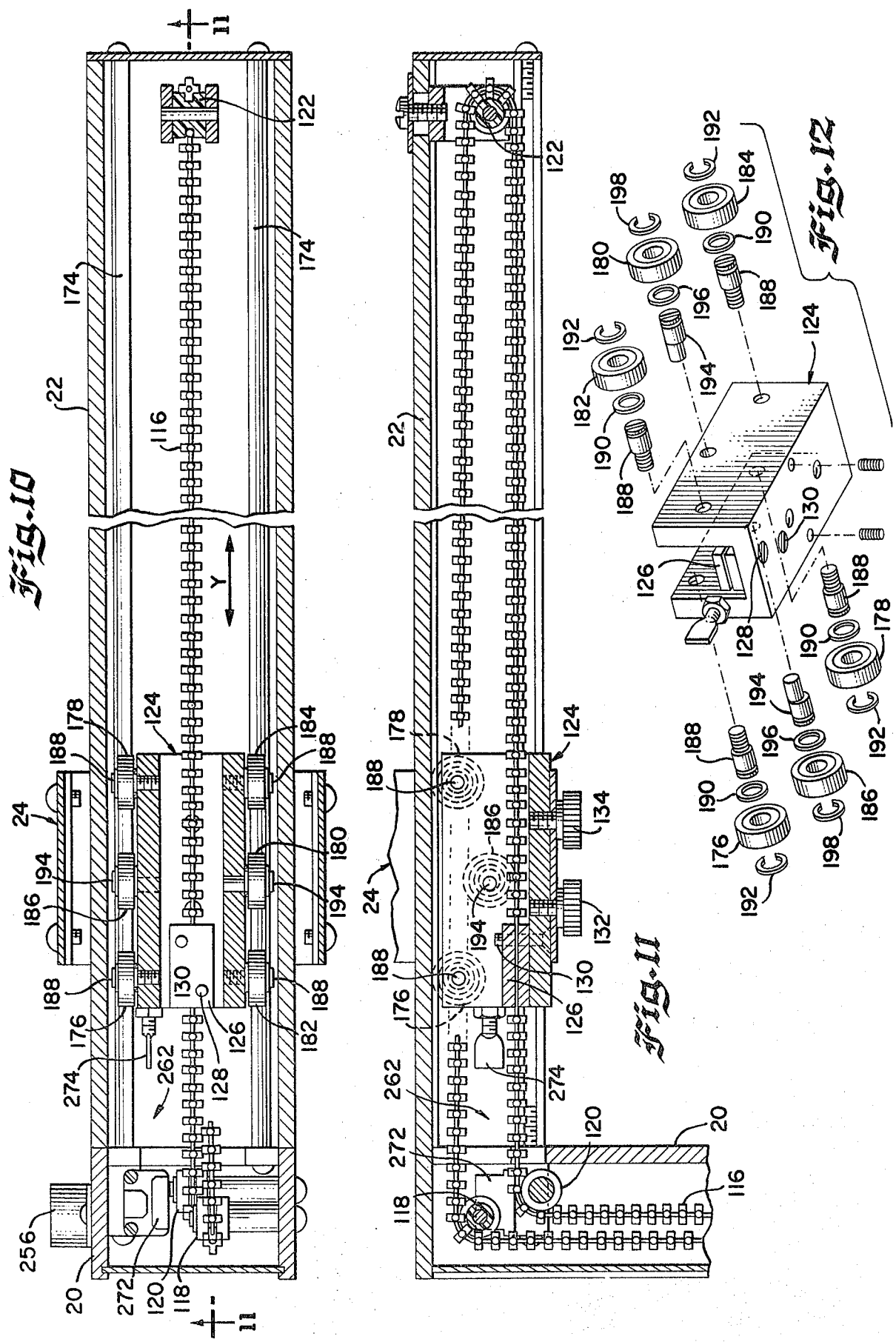

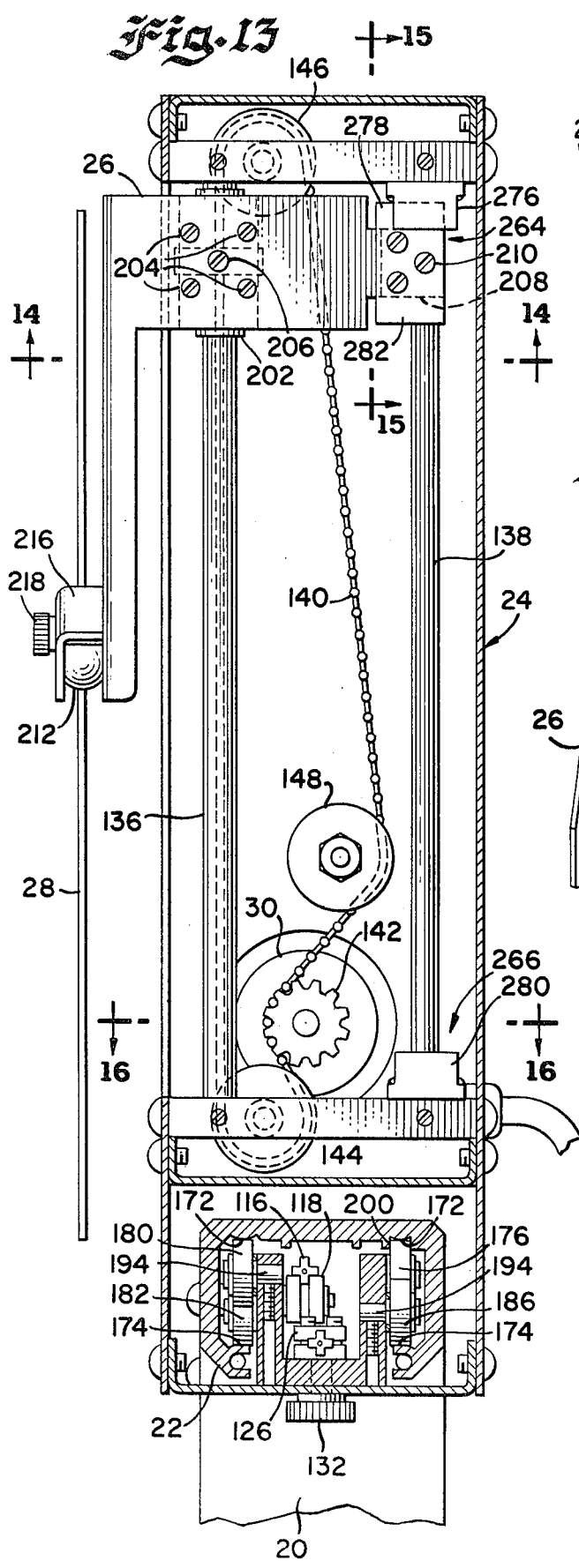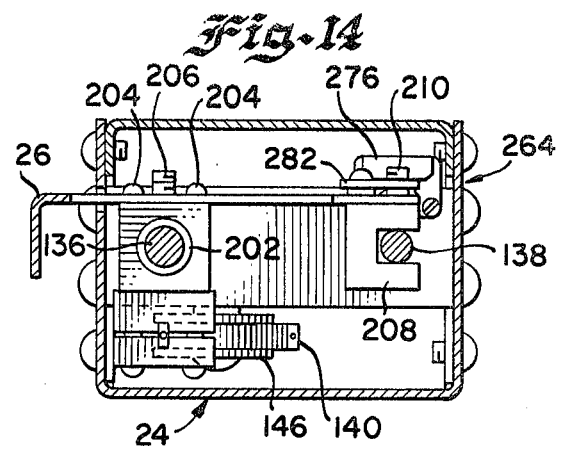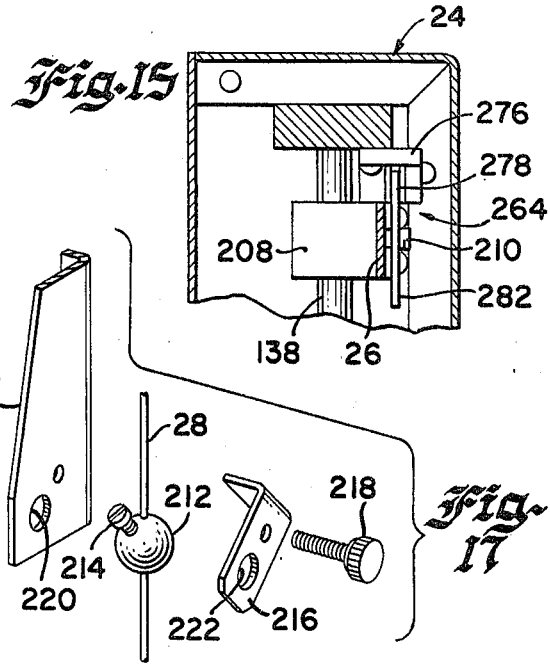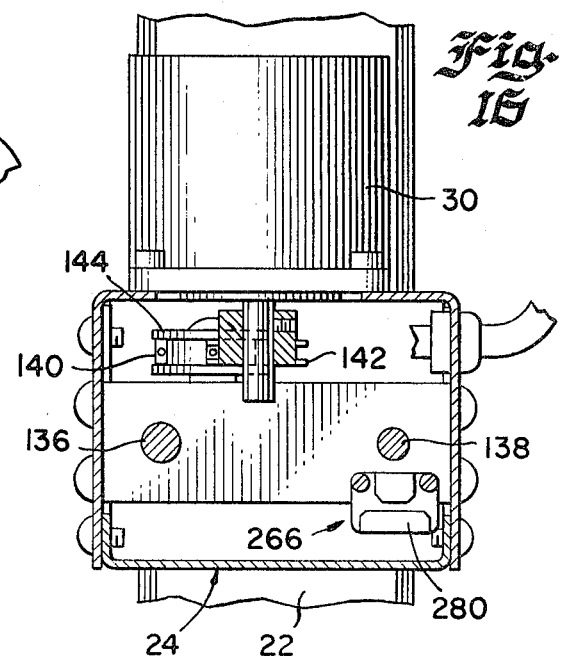

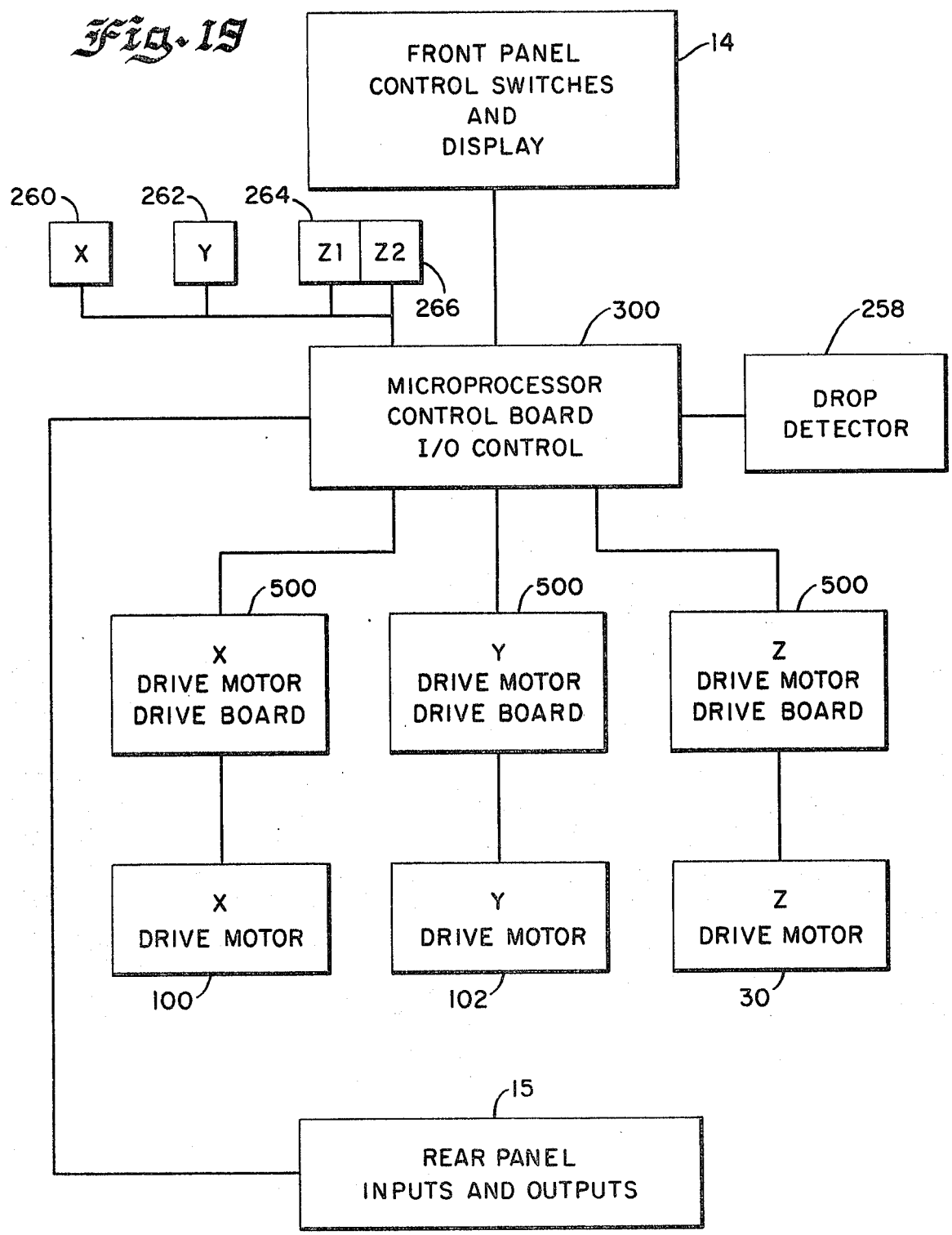
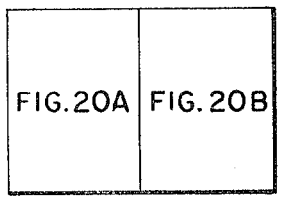

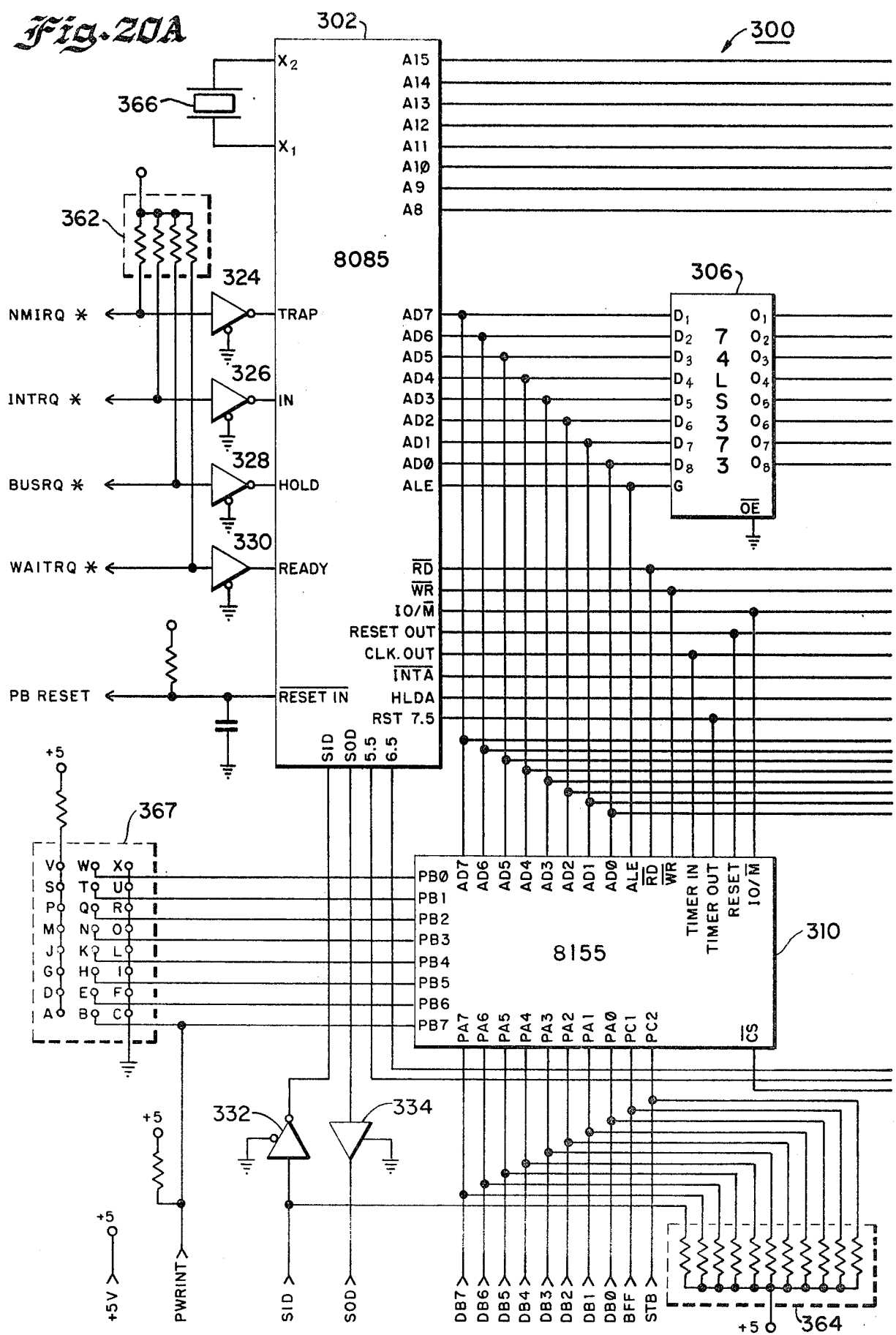

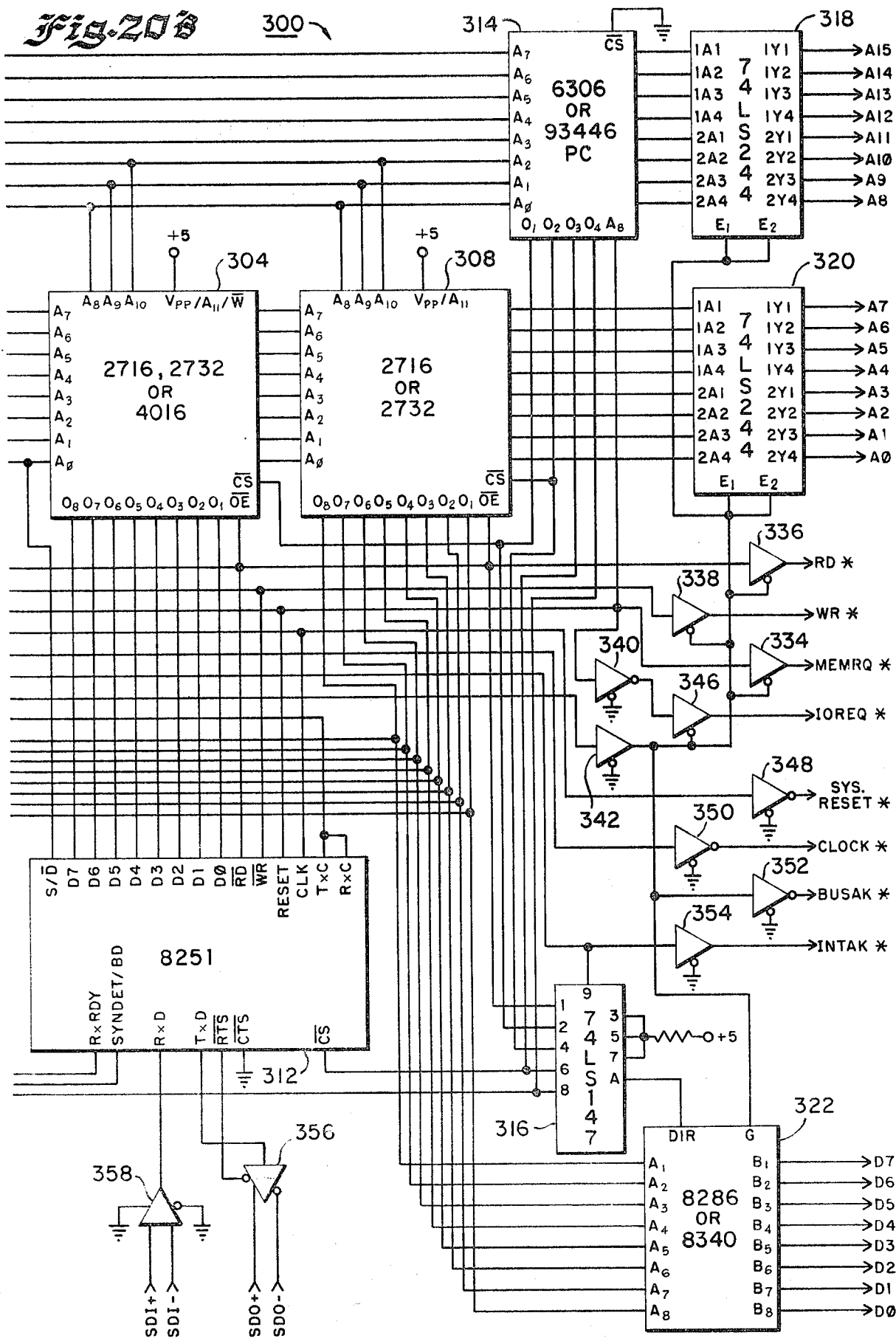

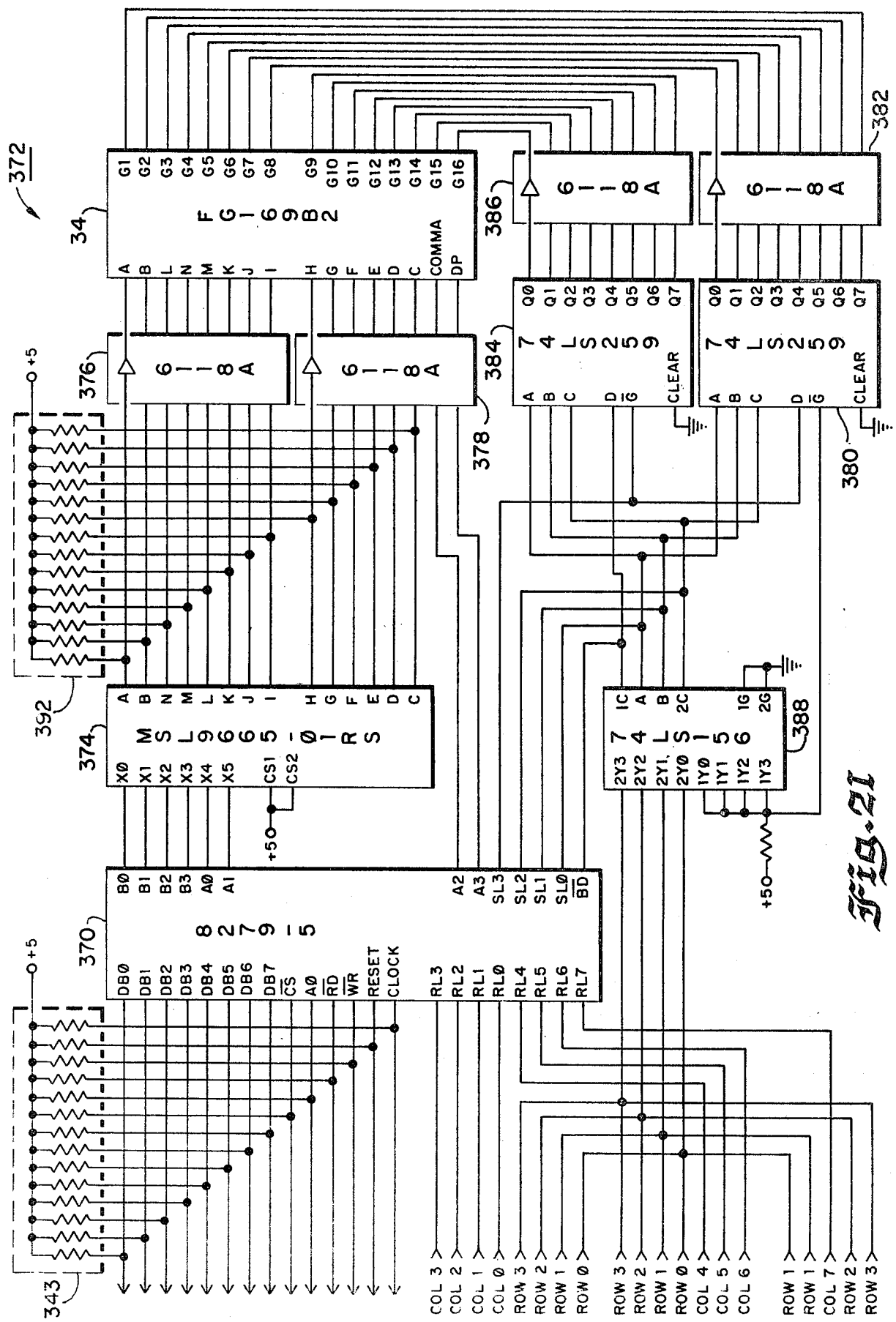

LIQUID HANDLING APPARATUS

BACKGROUND OF THE INVENTION

1. Field of the Invention

This invention relates generally to liquid handling apparatus, and more particularly to a liquid handling apparatus that is capable of several modes of operation, including fractionating, sampling, dispensing, diluting and other functions.

2. Description of the Prior Art

Various liquid handling systems are known. One of the most common of such liquid handling systems is a fractionator which is designed to deposit a predetermined volume of a particular liquid into each of an array of containers, such as test tubes, disposed in a rack located beneath the dispensing tube of the fractionator.

Other liquid handling devices such as dispensers, samplers and diluters are also known; however, all of them are limited in their capabilities, thus requiring different devices to be used for different applications. Moreover, the sampling or dispensing tube in such devices is limited in its movement capability, with most of such devices having liquid handling tubes or dispensing heads that are movable in only a few simple patterns. In addition, the liquid handling tubes or dispensing heads are movable in only two directions in a horizontal plane with respect to the array of containers, thus precluding the withdrawal of liquid from one container for deposit into another.

SUMMARY OF THE INVENTION

Accordingly, it is an object of the present invention to provide an improved liquid handling apparatus that overcomes many of the disadvantages of the prior art devices.

It is another object of the present invention to provide an improved liquid handling device that has a liquid handling tube or dispensing head that is movable in three directions with respect to an array of containers.

It is another object of the present invention to provide a microprocessor controlled liquid handling device that may be readily programmed to provide a wide variety of liquid handling functions.

It is yet another object of the present invention to provide a liquid handling apparatus that is capable of moving the liquid handling tube or dispensing head with great precision and in a wide variety of patterns.

It is still another object of the present invention to provide an improved liquid handling apparatus that can be readily programmed via a simple interactive keyboard input, or controlled by an external computer or console.

It is yet another object of the present invention to provide a liquid handling apparatus capable of communicating with various external devices such as, for example, pumps, display devices, computers and other support hardware.

It is yet another object of the present invention to provide a liquid handling device that has great mechanical strength and rigidity that is achieved with relatively simple mechanical construction.

In accordance with a preferred embodiment of the invention, there is provided a liquid handling device that employs three drive motors, preferably stepping motors, capable of moving the liquid handling tube or dispensing head in three mutually perpendicular directions with respect to an array of containers such as test tubes or the like. The three stepping motors are controlled by microprocessor circuitry that can be readily programmed by interactive controls located on a front panel of the apparatus, or by an external source such as a computer. The liquid handling apparatus according to the invention can be programmed to provide various functions, such as fraction collection, sampling, dispensing, diluting, or the like, and may be further programmed to provide various patterns of movement of the sampling or dispensing tube to accommodate various sizes and numbers of containers.

In order to provide extreme mechanical rigidity and accuracy of positioning of the tube, all of the moving components are suspended from a rigid plate by a plurality of rods and rollers which movably support a rigid extruded mast and boom, the latter containing a carriage movable in a direction perpendicular to the direction of motion of the mast and boom. The carriage located within the boom may be used to support the liquid handling tube directly, or alternatively, to support a gantry that has a vertically movable device holder may be carried by the carriage if vertical motion of the liquid handling tube is desired.

BRIEF DESCRIPTION OF THE DRAWING

These and other objects and advantages of the present invention will become readily apparent upon consideration of the following detailed description and attached drawing, wherein:

FIG. 1 is a front elevational view of the liquid handling apparatus according to the invention;

FIG. 2 is a plan view of the liquid handling device according to the invention, partially in cross section, taken along line 2—2 of FIG. 1;

FIG. 3 is a partial left side elevational view of the system according to the invention;

FIG. 4 is a partial rear elevational view of the system according to the invention;

FIG. 5 is a partial sectional view of the system according to the invention, taken along line 5—5 of FIG. 3;

FIG. 6 is a partial sectional view taken along line 6—6 of FIG. 3 showing the Y-direction drive motor;

FIG. 7 is a partial cross sectional view taken along line 7—7 of FIG. 3 showing the extraction drive motor;

FIG. 8 is a partial perspective view of the apparatus according to the invention showing the X-direction carriage and Y-direction drive motor;

FIG. 9 is a partial cross sectional view taken along line 9—9 of FIG. 6 showing the Hall effect home position sensor arrangement;

FIG. 10 is a partial cross sectional view of the device according to the invention taken along line 10—10 of FIG. 1 showing the cable car located within the boom;

FIG. 11 is a partial cross sectional view taken along line 11—11 of FIG. 10;

FIG. 12 is an exploded perspective view of the cable car illustrated in FIGS. 10 and 11;

FIG. 13 is a partial sectional view taken along line 13—13 of FIG. 1 showing the components within the gantry;

FIG. 14 is a sectional view taken along line 14—14 of FIG. 13;

FIG. 15 is a partial sectional view taken along line 15—15 of FIG. 13;

FIG. 16 is a partial sectional view taken along line 16—16 of FIG. 13;

FIG. 17 is a partial exploded perspective view of the tube supporting mechanism;

FIG. 18 is a partial cross sectional view taken along line 18—18 of FIG. 2 showing the table drain arrangement;

FIG. 19 is a functional block diagram of the electronic control and drive circuitry of the liquid handling apparatus according to the invention;

FIGS. 20A, 20B and 21 are detailed schematic diagrams of the electronic control circuitry of the device according to the invention;

FIG. 22 shows the relationship between FIGS. 20A and 20B of FIG. 20; and

DETAILED DESCRIPTION OF THE PREFERRED EMBODIMENT

Figure 23:
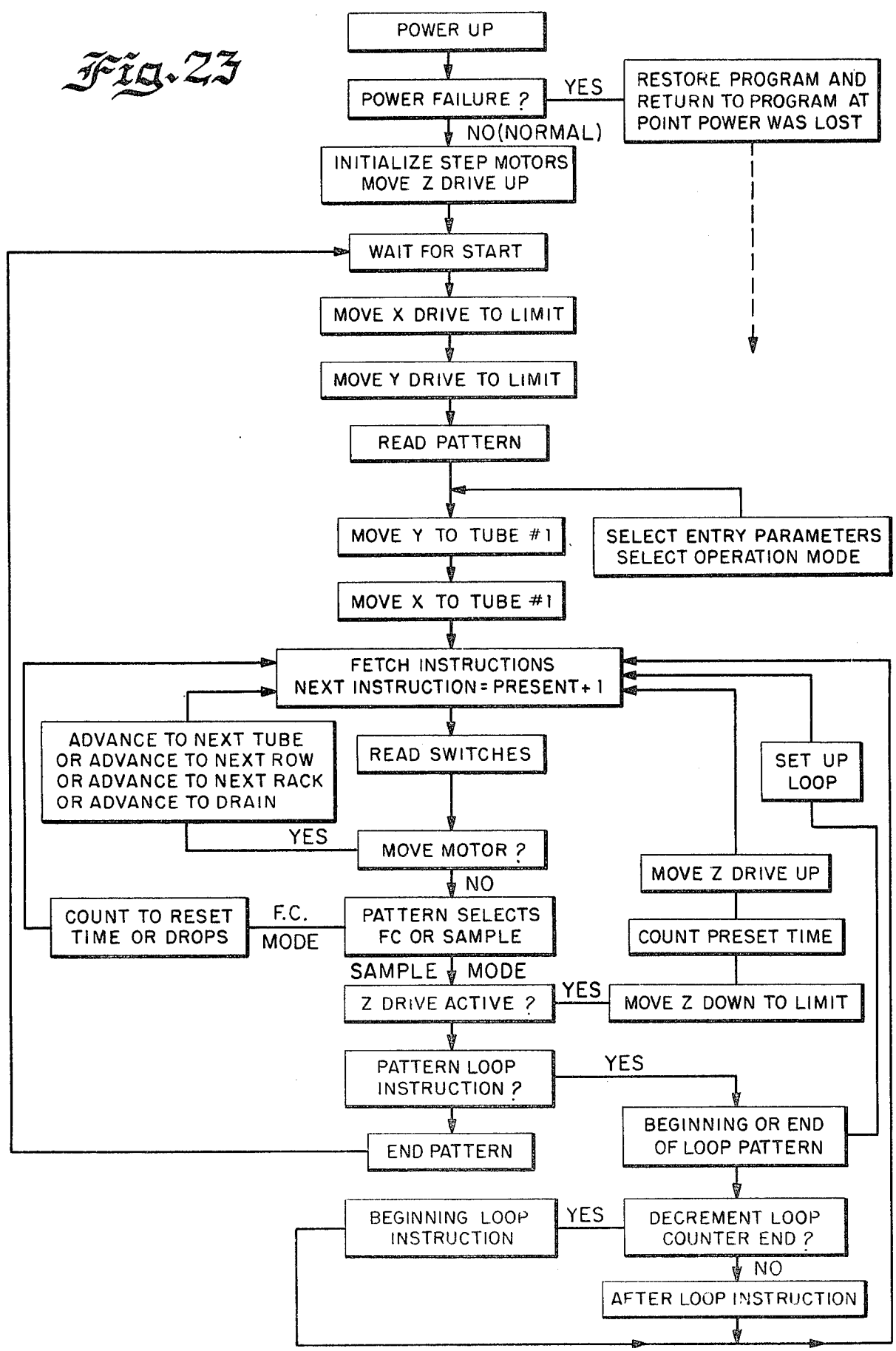
FIG. 23 is a logical flow chart illustrating the sequence of operation of the logic circuits of the liquid handling device according to the present invention.

Referring now to the drawing, with particular attention to FIG. 1, there is shown a front elevational view of the liquid handling apparatus according to the invention generally designated by the reference numeral 10. The liquid handling apparatus 10 includes a base 12 having a front control panel 14, a rear panel 15 and a table 16 designed to support a rack 18. A mast 20 extends upwardly from the base 12, and a boom 22 extends laterally from the mast 20. Optionally, a gantry 24 may be movably affixed to the boom 22. The gantry 24 includes a device holder 26 which supports a tube 28 and a Z-direction motor 30. A power on/off switch 32 is disposed on the control panel 14 as is an alphanumeric display 34. A keyboard 36 containing twelve keys designated as 1–9 and 0 as well as clear and enter keys disposed on opposite sides of the zero is also located on the front panel 14. Other keys grouped in two groups 38 and 40, whose function will be described in a subsequent portion of the detailed description, also serve to control the operation of the liquid handling device according to the invention.

The rack 18 or a plurality of racks 18 (FIG. 2) serve to hold a plurality of receptacles, such as test tubes, and are secured together via a pair of bars 40 and a plurality of screws 42. The racks 18 are in turn secured to a pan 44 by four locating pins 46 extending upwardly from the plate 44. The locating pins 46 are unequally spaced to assure that the racks 18 may be oriented in only one orientation. The pan 44 is located on a plate 45 by four locating pins 48 extending upwardly from the plate 45. The plate 45 is in turn affixed to the table 16 by three downwardly extending pins 49 and a shoulder 51 on one of the pins 48. As in the case of the locating pins 46, the locating pins 48 and 49 are also unequally spaced to assure that the pan 44 and the plate 45 can be located in only a single orientation with respect to each other and with respect to the table 16.

The keyboard 76 contains twelve keys. Ten of the keys are designated by the numerals 1 through 0 as indicated in FIG. 1. In addition, two keys designated as "CLEAR" and "ENTER" are disposed to the left and right of the 0 key, respectively. These keys are used to enter numerical data defining, for example, the number of drops to be placed in each receptacle, the amount of time to be spent over each receptacle, the number of receptacles to be filled, and the starting and stopping point along the racks for a particular operation, and other functions. In addition, the twelve keys forming the keyboard 36 are used to select the mode of operation of the device. To aid the operator in selecting the mode of operation, the keys labelled 1-6 also have their function selection designations printed above the respective push button. For example, the switches 1 and 2 have the word "FRACTIONATOR" printed above them to indicate that they are used to select one of two different modes of fractionation. Similarly, the push button designated by the number 3 has the word "SAMPLER" disposed in the area above it, the number 4 push button is captioned with the word "DISPENSER", the number 5 push button is captioned "AUTO DILUTER" and the number 6 push button is designated as "OPTION". In addition, the number 7 push button is labelled with the word "YES" and the number 9 push button is captioned with the word "NO" to enable questions posed by the device via the alphanumeric display 34 to be answered by the operator.

The keyboard 40 is used to initiate, terminate, or alter the function being performed by the liquid handling device according to the invention. To facilitate this function, the keyboard 40 contains 7 push buttons 52, 54, 56, 58, 60, 62 and 64. These push buttons are captioned with descriptive statements indicative of their function, such as "NEXT TUBE", "NEXT ROW", "NEXT RACK", "DRAIN", "START", "STOP", and "CANCEL", respectively. Thus, these push buttons can be used to control the stepping of the tube or head manually, to start and stop the operation of the device, to cancel an existing stepping sequence and to cause the device to drain the liquid being dispensed.

Finally, the keyboard 38 comprising a pair of push buttons 66 and 68 is used in conjunction with the keyboard 36 to control the entry of data into the device or to edit an already existing program. In this connection, the push button 68 is captioned "ROLL DISPLAY" and serves to display the individual instructions of a previously programmed program on the alphanumeric display 34, and sequentially to display the various instructions one-by-one on the display 34 each time the push button 68 is depressed. The push button 66 is captioned "EDIT" and permits any one of the instructions displayed on the display 34 to be altered by depressing the EDIT button 66 and entering new data via the keyboard 36.

In operation, after the device has been plugged into a source of electrical power, the internal microprocessor program is started at the beginning, and the display will sequentially display various prompting questions requesting the operator to enter certain data. In a typical program, after the device has been energized and turned on, the display will prompt with the word "PATTERN?". In response to this question, the machine expects an entry identifying the physical attributes of the rack 18 being used to enable the device to select the step size between test tubes, as well as the total number of test tubes being held by the rack. This identification can be conveniently accomplished by stamping a number on the particular rack being used and entering that number via the keyboard 36 to identify the particular rack being used. The dimensions of the rack will be stored in the memory of the device and retrieved when the rack identifying number is entered. After the rack identifying number is entered, the "ENTER" key is depressed to enter the rack identifying number with the device.

After the rack number indicating the desired pattern has been entered, the display will indicate the prompt word "MODE?". In response to this prompting, the operator depresses one of the push buttons captioned "FRACTIONATOR" to select one of the fractionator modes, or may depress one of the push buttons captioned "SAMPLER", "DISPENSER", "AUTO DILUTER", or "OPTION". If the user has depressed the OPTION button, thereby ordering an optional mode, the display will prompt the user for an option number, defining the option, which must then be entered. If any of the other function selecting push buttons have been depressed, the alphanumeric display 44 will prompt the user to enter various essential parameters necessary for the device to carry out the selected mode of operation.

In the fraction collector mode of operation, either a drop mode or a time mode may be selected by depressing one of the push buttons captioned 1 or 2. If the push button captioned 1 is selected, the drop mode is selected, and if the push button captioned by the number 2 is selected, the time mode is selected. If the drop mode has been selected, the actual number of drops to be put into each tube must be entered via the keyboard 36. If the time mode has been selected, the actual time per tube, or the actual time between tube advances must be entered. Such times entered as minutes and seconds, with two digits being allowed for minutes and two digits for seconds. If only two digits are entered, it is presumed that seconds have been entered. The drop or time parameters in the fraction collector mode are essential parameters and must be entered before the device can be made to operate.

In addition to the essential time or drop parameters, several optional parameters are permitted in the fractionator mode. For example, the total number of tubes desired for the collection may be entered when prompted by the word "T/TUBE" on the display. If not entered, the maximum number of tubes contained in the rack corresponding to the selected pattern is used as the value of the total number of tubes.

Another optional parameter is the start delay, prompted by the words "START/DLY" on the alphanumeric display 34. The start delay sets a timer so that the fraction collector will start at a preset time after the start button (or a remote start) has been activated. The time is entered as hours, minutes, and seconds via the keyboard 36. If no time is entered, no delay is introduced, and collection begins immediately after the start button is depressed.

A remote advance delay prompted as "ADV/DLY" in the alphanumeric display 34 is used when an integrator or other remote device signals a test tube advance. The advance delay programs a delay, via the keyboard 36 that permits the advance to be delayed by the preset time to compensate, for example, for the delay time required for the liquid to flow through the tubing between, for example, the detector and collector. In addition, inputs and outputs, to be discussed in a subsequent portion of the specification, are provided to permit the device to be remotely started and remotely advanced, and an output is provided by the device each time the dispensing head or tube advances. Auxiliary power that is turned on during a run and turned off at the end of the run is also provided to control an external pump or other external device. In addition, a second auxiliary power output that is off during tube advance and at the end of the run is provided. This power source may be utilized to control an auxiliary pinch valve.

In the diluter mode of operation, the device picks up a sample from a test tube in a first rack and dispenses the sample with diluent into a test tube in a second rack. The outside of the probe is then rinsed at a rinse station, and the next sample is taken. In the diluter mode, a standard diluter pattern between two racks is used; however, two essential parameters, namely, rinse time and stroke length are required. The rinse time parameter is entered in response to a prompt word "RINSE/T" and is entered as the time in the rinse position, or as zero, in which case the rinse function is skipped. The stroke length parameter sets the amount of required vertical direction, or Z-direction movement and is set to provide approximately 5-6 mm clearance above the tubes. An optional parameter T/TUBES indicates the number of samples to be diluted if the number of samples is less than the total number of tubes in the rack.

In the dispenser mode of operation, the device according to the invention operates in conjunction with an external dispenser that dispenses a preset volume of liquid into each tube in the pattern sequence. The essential parameter in the dispenser mode is the time between dispenses, DISP/T, which is set by entering the time in minutes and seconds between dispenses via the keyboard 36. This time should not be shorter than the cycle time of the external dispenser; however, the dispense time can be controlled remotely by the cycling of the dispenser to cause the system to operate at the fastest possible rate. If the device is controlled by the dispenser, the dispense time should be set to zero.

Optional parameters include the total number of tubes, T/TUBES, which may be entered if the quantity of tubes to be filled is less than the maximum number of tubes in the rack. Also a repeat dispense, RPT/DISP, may be used if more than one dispense volume is to be dispensed into each tube.

In the sampler mode, the device according to the invention is used with an auxiliary pump, such as a peristaltic pump for sucking samples from the sample pipette, and for transferring the solution to the active test point. Once the pattern and mode have been entered, additional essential parameters of sample time (S/TIME), transfer time (TRANS/TIME) and pause time (PAUSE/TIME) must be entered. The sample time sets the volume of the sample and is dependent on flow rate and time. The transfer time is the time required to transfer the sample to the test point if the sample size is smaller than the transfer tubing volume. The pause time is the waiting time after the sample has been transferred and allows for settling or reaction of the transfer, or can be used to slow the sample transfer for other reasons. A stroke length parameter so that the probe will clear the top of the test tube by 5-6 mm is also required.

Optional parameters air time (AIR/TIME) and rinse time (RINSE/TIME) may also be entered. The air time parameter allows the insertion of an air bubble after each sample or after a rinse. The rinse time parameter allows additional time beyond the transfer time for large rinse volume.

In order to provide the various functions described above, the device according to the invention must be capable of moving the dispensing or sampling tube very precisely in three mutually perpendicular directions, and must include control circuitry capable of storing a variety of programmed instructions and utilizing those instructions precisely to control the operation of three motors, preferably stepping motors that are used to move the liquid handling tube or dispensing head in the three mutually perpendicular directions. In order to move the tube or head in two mutually perpendicular horizontal directions, there is provided a pair of motors, preferably stepping motors 100 and 102 (FIG. 3) within the base 12 of the device. The stepping motor 100, hereafter referred to as the X-drive motor, is rigidly affixed to the base 12 by means of a mounting plate 104 (FIGS. 3 and 7) and serves to drive the tube or head in a horizontal direction, hereafter called the X-direction, parallel to the sides of the base 12. The stepping motor 102 is affixed to a mounting bracket 106 which is in turn affixed to a car 108 (FIGS. 3, 6 and 8) that is mounted within the base 12 and movable in the X-direction. A drive belt, such as, for example, a timing belt 110 (FIG. 2) is attached to the car 108 by a pair of screws 107 and 109 and a block 111, and engages a sprocket 112 on the shaft of the stepping motor 110 in order to permit the stepping motor 100 to drive the car 108 in the X direction. The mast 24 is affixed to the car 108 and is moved in the X direction by the movement of the car 108. A sprocket 114 is affixed to the drive shaft of the Y-direction motor 102 and engages a second belt, such as, for example, a timing belt 116 which extends through the mast 20 and the boom 22 (FIGS. 3, 10 and 11). The belt 116 is guided through the boom 20 and the mast 22 by three grooved rollers 118, 120 and 122 (FIGS. 10 and 11). A carriage 124 is movably mounted within the boom 22 for movement in the Y direction, which is parallel to the direction of elongation of the boom 22 as well as to the front and back panels of the base 12. The carriage 124 is affixed to the belt 116 by a plate 126 and a pair of screws 128 and 130 in order to permit the carriage 124 to be moved in the Y direction by the Y-direction stepping motor 102.

If only horizontal motion of the tube 28 is required, the tube or head 28 may be attached to the carriage 124 by a bracket or other suitable holding device (not shown) affixed to the carriage 124 by means of thumb screws 132 and 134 (FIG. 11). In this case, movement in the X direction would be achieved by operating the X-direction drive motor 100 in order to move the entire assembly comprising the mast 20, the boom 22 and the carriage 124 in the X direction. Movement in the Y direction would be achieved by energizing the Y-direction drive motor 102 to cause the motor 102 to move the carriage 124 in the Y direction within the boom 22. Such two-directional motion is sufficient for many liquid handling functions, such as, for example, fractionating and dispensing. However, in other modes of operation, such as, for example, sampling and diluting, three-axis movement of the tube or head 28 is required. This third axis or Z-direction movement is provided by attaching the gantry 24 to the carriage 124 by means of the thumb screws 132 and 134.

The details of the gantry 24 are best illustrated in FIGS. 13-16 and show the device holder 26 being slidably supported within the gantry 24 by a pair of rods 136 and 138. As in the case of the X-direction car 108 and the Y direction carriage 124, the holding device is moved by a drive belt 140 which may be, for example, a timing or sprocket belt similar to the drive belts 110 and 116. Also, a sprocket 142 is affixed to the shaft of the Z-direction drive motor 30 and engages the drive belt 140. The drive belt 140 is supported with the gantry 24 by a pair of pulleys 144 and 146 located near the limits of the travel of the device holder 26, and by an idler pulley 148 located within the gantry 24.

Because of the operational flexibility of the system according to the invention, and because of the need to position the tube precisely over virtually any point above the table 16, the various moving parts of the system must be precisely fabricated and accurately and rigidly assembled in order to assure smooth, precise movement. In order to provide the required rigid structure, the table 16 may be fabricated, for example, from a heavy sheet of sheet steel, typically on the order of ⅛ inch thick. Such a table provides a stable platform from which all of the moving parts of the X-, Y- and Z-drive mechanisms can be suspended. The suspension is achieved by a pair of heavy plates 150 and 152 (FIG. 3) that are screwed or otherwise suitably fastened to the table 16. The plates 150 and 152 may be fabricated, for example, from ⅜ inch thick aluminum plates, and used to support a pair of guides 154 and 156 (FIGS. 3, 5, 6, and 7) which may be, for example, a pair of steel bars of circular cross section ¾ inch in diameter.

To assure smooth, precise movement of the car 108 with respect to the guides 154 and 156, in accordance with an important aspect of the invention, the car 108 is supported with respect to the guide 154 by three guide rollers 158, 160 and 162 (FIGS. 5, 6 and 8) circumferentially spaced about the guide 54, preferably at 120° angular spacings. The use of such circumferentially spaced rollers, such as the guide rollers 158, 160 and 162, which to further reduce friction may be ball bearing rollers, precisely locates the car 108 in both the horizontal and vertical directions with respect to the table 16. Consequently, since the car 108 is precisely located in the Y and Z directions for movement in the X direction with respect to the table 16, all that is required is to maintain the car 108 located in the proper angular orientation with respect to the table 16. This function is provided by a pair of guide rollers 164 and 166 (FIGS. 5, 6 and 8) spaced at diametrically opposed locations about the guide 156. Thus, through the use of only five guide rollers, the car 108 is accurately positioned with respect to the table 108. The system also provides for a fine adjustment of the guide rollers with respect to the guides 154 and 156. This adjustment is accomplished by a pair of screws 168 and 170 which move the respective guide rollers 162 and 166 radially with respect to the respective guides 154 and 156 in order to adjust the clearance between the guides and the guide rollers to provide an optimum balance between accuracy of positioning and ease of movement.

The mast 20 is rigidly attached to the car 108 by four mounting screws 172 (best seen in FIG. 3). The boom 22 is, in turn, welded to the mast 20 to provide a very rigid structure. Consequently, the car 108, the mast 20 and the boom 22 move together as a unit, thus allowing the boom 22 to be positioned nearly as accurately as is the car 108. In order to preserve this accuracy, the carriage 124 must be accurately positioned within the boom 22. This is accomplished by providing a pair of upper tracks 172 and a pair of lower tracks 174 (best seen in FIG. 13) inside the boom 22. If the boom 22 is extruded, as in the illustrated embodiment, these tracks can be formed at the time the boom is extruded.

In order to provide smooth motion, as well as good positioning accuracy for the carriage 124, in accordance with an important aspect of the present invention, there are provided three upper guide rollers 176, 178 and 180 as well as three lower guide rollers 182, 184 and 186 (FIGS. 10-12) on the carriage 124. The upper guide rollers 176, 178 and 180 provide a stable three-point contact with the upper track 172, while the lower guide rollers 182, 184 and 186 provide a three-point contact with the lower tracks 174. The guide rollers 176, 178, 180, 182, 184 and 186 may be ball bearing type rollers to minimize rolling friction, and the leading and trailing upper rollers 176 and 178, as well as the leading and trailing lower rollers 182 and 184 may be readily affixed to the body of the carriage 124 by four threaded axles 188, spacers 190 and C-washers 192. However, in order to minimize vertical play in the travel of the carriage 124, and in accordance with another important aspect of the present invention, the central upper roller 180 and the central lower roller 186 are affixed to the body of the carriage 124 by a pair of offset axles 194, spacers 196 and C-rings 198. The offset axles 194 are press fit into the body of the carriage 124, and by rotating the axles 124, the central upper and central lower rollers 180 and 186 can be moved vertically in order to level the carriage 124 and to optimize the clearance between the six guide rollers and the tracks 172 and 174 of the boom 122. Lateral support for the carriage 108 is provided by a guide 200 (FIG. 13) disposed adjacent to one of the tracks 172 extruded at the same time that the boom 22 is extruded.

As previously discussed, the combination of the X-drive motor 100 and the Y-drive motor 102 serve to drive the mast 20, boom 22 and carriage 124 to provide accurate motion of the carriage 124 with respect to the table 16. Also, as previously discussed, if only X-Y motion is required, a bracket may simply be secured to the carriage 124 via the thumb screws 132 and 134. Also, as previously discussed, if Z direction, or vertical motion, is required, the gantry 24 may be secured to the carriage 124 via the aforesaid thumb screws 132 and 134 in order to provide such vertical motion. However, to maintain positioning accuracy, the vertical motion must be accomplished without permitting an excess of horizontal motion. Consequently, in the gantry used in conjunction with the device according to the present invention, the device holder 26 is supported by the guides 136 and 138 (FIG. 13), and X direction and Y direction motion is limited by utilizing a slide bearing 202 disposed over the guide 136 and affixed to the device holder by a plurality of screws 204. Since the mass of the apparatus supported by the device holder 26 is much less than the mass supported by either the car 108 or the carriage 124, guide rollers are not necessary to support the device holder 26, and a slide bearing, such as the slide bearing 202, preferably made of bronze is sufficient. However, due to machining tolerances, it is advisable to allow the clearance between the slide bearing 202 and the guide 136 to be adjusted. Accordingly, an adjusting screw 206 analogous to the adjusting screws 168 and 170 is provided. The adjusting screw 206 may be fabricated from a low coefficient of friction material, preferably a plastic, such as nylon or Teflon, and extends through the slide bearing 202 to contact the guide 126. Thus, by appropriately adjusting the adjusting screw 206, the clearance between the slide bearing 202 and the guide 136 may be appropriately adjusted.

The guide 136 and the slide bearing 202 cooperate to locate the device holder 26 in the X- and Y-horizontal directions, but, as is readily apparent, the device holder 26 is not precluded from rotating about the guide 136. Consequently, the second guide 138 cooperates with a second open ended slide bearing 208 that slidably engages the guide 138. The bearing 208 may be fabricated from any suitable material, and it has been found that a plastic material, such as nylon or Teflon is suitable. Also to control the clearance between the bearing 208 and the guide 138, a second adjusting screw 210, which may be made of a similar material to the adjusting screw 208 is provided.

Finally, although it is possible to affix the tube 28 to the device holder 26 or to the carriage 124 by a simple bracket or the like, it has been found desirable to permit a certain degree of adjustment of the position of the tube 28 with respect to the device holder 26 and carriage 124. It has been found that a simple, convenient and flexible way to provide such adjustment is simply to affix the tube 28 to a sphere 212, for example, by means of a set screw 214. The sphere 212 may then be retained between the device holder 26 and a clamp 216 by means of a thumb screw 218. By providing a pair of apertures 220 and 222 having diameters smaller than the diameter of the sphere 212 in the holder 220 and clamp 216, and by fabricating the sphere 212 from a material having a relatively low coefficient of friction, such as a plastic material such as nylon or Teflon, the sphere 212 may be securely retained between the device holder 26 and the bracket 216, and yet may be angularly oriented to position the tube 28 as required.

As previously discussed, the liquid handling apparatus according to the invention is designed for use with external devices, such as external computers as well as external pumps and dispensers. Accordingly, there is provided on the rear panel 15 of the base 12 a plurality of interfaces for the purpose of controlling and communicating with such external devices. In this connection, there are provided a pair of auxiliary power outlets 230 and 232 into which various auxiliary equipment may be plugged. The auxiliary outlets 230 and 232 may either be energized continuously, or may be controlled by the logic circuitry within the liquid handling device to apply electrical power to the external devices only as necessary.

In addition, there are provided various input and output connectors 234, 236 and 238 which serve to control the external devices and receive information therefrom. The connector 238 is a contact closure connector and is connected to the contacts of a relay or the like within the base 12 of the liquid handling device. Thus, an external device can be controlled by the closure of the contacts of the relay within the base 12. In addition, the connector 238 is connected to circuitry within the base 12 that is responsive to an external contact closure and serves to make the liquid handling device responsive to the closure of an external circuit such as a relay contact or switch. This enables the operation of the liquid handling device to be controlled by such an external switch closure. For example, in the dispensing mode, the dispense time can be controlled by the cycling of the dispenser so that the liquid handling device can be made to operate at the cycle time of the dispenser.

Connectors 234 and 236 are binary data interfaces with the connector 234 being capable of receiving and outputting binary data in parallel form and the connector 236 being capable of receiving and outputting such binary data in serial form. These connectors permit the liquid handling device to communicate with or be controlled by an external computer or the like.

A power input plug 240 plugs into a power line cord (not shown) to provide electrical power to the device via a fuse 241. A system rest switch 242 is used to rest the system when power is first applied. An indicator light 244 serves as a low battery condition indicator to indicate when an internal battery (not shown) used to maintain the memory active during a power interruption is low. A gantry holder 246 serves to store the gantry 24 when it is not in use.

A drain aperture 248 is provided to permit a drain hose 250 (FIG. 18) to be attached to a drain 252 in the plate 44. The drain 252 provides a convenient way to dispose of excess and waste liquids simply by programming the device to dispense such excess and waste liquids directly into the drain. In addition, the drain 252 serves to dispose of spills conveniently.

Finally, a 25-pin connector 254 (FIG. 3) is used to provide an electrical interconnection between the stepping motor 30 of the removable gantry 24. A second connector 256 on the mast 20 provides an interconnection between the logic circuitry of the liquid handling device and a drop counter (not shown) located near the dispensing head or tube 28.

The layout of the electronic control circuitry for the liquid handling system according to the present invention is generally illustrated in the block diagram of FIG. 19. The front control panel 14, which houses control switches for applying input data and the display, is electrically coupled to a microprocessor control board 300 which includes input and output control circuitry. The microprocessor control board 300 receives data from the front panel 14 and drives the X-drive motor 100, the Y drive motor 102 and the Z-drive motor 103 via three motor drive boards 500 in accordance with the instructions received from the control switches on the front panel 14 as well as from any input signals received via the inputs on the rear panel 15. The outputs for controlling auxiliary equipment on the rear panel 15 are also coupled to the microprocessor control board 300. A drop detector 258 (not shown in the mechanical drawings) is used when the liquid handling system accordingly to the invention is used in the drop counting mode. The drop detector 258 is mounted in proximity to the dispensing tube and provides an indication of the number of drops dispensed to the microprocessor control board 300.

In addition, four sensors 260, 262, 264 and 266 are used to sense the position of the X-direction car 108, the Y-direction carriage 124 and the two extreme Z-direction positions of the device holder 26, respectively. The X-position sensor 260 is used to sense the home or zero position of the X-direction car 108, and utilizes a Hall effect sensor 268 mounted on the car 108 (FIGS. 1 and 9) that engages a spade 270 affixed to the supporting plate 150 when the car 108 is in the home or zero position. The engagement of the spade 270 by the Hall effect device 268 causes the impedance of the Hall effect device 268 to change, thereby providing an indication to the microprocessor control board 300 that the car 108 is in the home position. Since the X-drive motor 100 is a stepping motor, once the home position has been established, the car 108 can be moved to any position in the X direction by simply applying the appropriate number of pulses to the X-drive motor 100. This is because of the operational characteristics of the stepping motors and drive boards used in the present invention which cooperate to cause the drive shafts of the stepping motors to be incremented by a fixed increment each time a pulse is received from the microprocessor control board 300.

The Y-direction position sensor 262 comprises a Hall effect device 272 mounted in the mast 20 and a spade 274 (FIGS. 10 and 11) attached to the carriage 124. The operation of the Hall effect device 272 and the spade 274 is similar to that of the operation of the Hall effect device 268 and the spade 270, and serves to indicate the home or zero position of the carriage 124. As in the case of the X-direction car 108, once the home or zero position has been established, the carriage 124 can be positioned accurately in the Y direction by applying the appropriate number of pulses to the Y-direction drive motor 102.

Two position sensors are used to sense the position of the device holder 26 in the vertical or Z direction. The first position sensor 264 is mounted near the top of the gantry 24 and comprises a Hall effect device 276 and a blade 278 to indicate when the device holder 26 is at the top of the gantry 24. The second position sensor 266 comprises a second Hall effect device 280 mounted near the bottom of the gantry 26 that operates in conjunction with a second blade 282, which may be formed from the same piece of material as the blade 278, to indicate when the device holder is at the bottom of the gantry 26. Consequently, an upper home or zero point, as well as a lower home or zero point is established in order to permit the device holder either to be lowered a predetermined distance from the upper home or zero point, or to be raised a predetermined distance from the lower home or zero point, depending on the application or task being performed. As in the case of the car 108 and the carrige 124, the device holder 26 may be accurately positioned with respect to either the upper or lower home or zero point by appropriately selecting the direction of rotation of the Z-direction motor 30 and by applying the required number of pulses.

The microprocessor control board 300 is illustrated in greater detail in FIG. 20. The microprocessor control board 300 comprises, for example, an integrated circuit microprocessor 302, which may be, for example, a type 8085 microprocessor manufactured by Intel and other manufacturers. The microprocessor chip 302 operates in conjunction with several memories, including a memory 304 which may be a random-access memory, such as, for example, a type 4016 random-access memory or a programmable read-only memory such as a type 2716 or 2732 type programmable read-only memory. The memory 304 serves to store the program for the microprocessor 302, and is coupled to the microprocessor 302 via a latch 306. A memory 308, for example, a programmable read-only memory such as a type 2716 or 2732 memory is used to select the desired program from the memory 304. In addition, an input/output timer and random-access memory 310, which may be a type 8155 manufactured by Intel, is employed as is a serial-to-parallel converter 312. Also, a mapper PROM 314, for example, a type 6306 programmable read-only memory cooperates with a logic circuit 316, for example, a type 74LS147, and drivers 318 and 320, which may be type 74LS244, for the purpose of addressing external circuitry. Examples of the external circuitry referred to above include other circuit boards within the liquid handling device such as X-, Y- and Z-motor drive boards. Data is provided to and received from the external circuitry via a bidirectional driver 322, for example, a type 8286, or 8304 driver.

A plurality of amplifiers 324, 326, 328, 330, 332, 334, 336, 338, 340, 342, 344, 346, 348, 350, 352, 354, 356 and 358 serve as input and output drivers, to other devices such as an external computer. These amplifiers are connected either directly or indirectly to one of the inputs or outputs on the back panel 15. A pair of resistor networks 362 and 364 serve as pull-up resistors for the inputs of the amplifiers 324, 326 and 328 and for the outputs of the input/output timer/RAM 310, respectively. A quartz crystal 366 serves as a time base for the microprocessor 302.

The microprocessor 302 cooperates with the memories 304 and 308 to provide the appropriate data processing for performing the previously described functions. In addition, the microprocessor 302 cooperates with the read-only memory 314 which is programmed as an address mapper to determine which internal or external device is being addressed by the microprocessor 302. In this connection, the mapper 314 receives an eight-bit address A0-A7 and provides a five-bit word 01-04 and A8 to select preselected ones of the internal and external devices to be enabled by a particular address. The address information applied to the mapper is also passed on through the driver 318 to the external circuitry to effect the addressing.

The terminals AD0-AD7 of the microprocessor 302 serve both as input and output terminals, more specifically, they serve as address input terminals and data input and output terminals. Thus, the terminals AD0-AD7 serve to receive both address and data information from an external source and to provide data to other devices. The memory/input/output and timer circuit 310 provides memory and timer functions, and in addition, provides information from external devices, such as, for example, the X, Y and Z direction zero or home position sensors 260, 262, 264, 266 to the microprocessor 302 to provide an indication to the microprocessor 302 of the position of the sampler/dispenser tube with respect to the X-, Y-and Z-directions of movement. The universal synchronous/asynchronous receiver-transmitter 312, in cooperation with amplifiers 356, 358 and 360, serves to provide communication with external devices, such as, for example, an external computer. The bidirectional driver 322 provides data to external devices, when enabled by the device 316, to indicate that an external, rather than internal device is being supplied with data. Finally, control signals for the microprocessor 302 are received via the amplifiers 324, 326, 328 and 330, and control signals for the external circuitry are provided via the amplifiers 336, 338, 340, 342, 344, 346, 348, 350, 352 and 354. In addition, when more than one liquid handling device according to the invention is being controlled from one or more computers, it is desirable to provide each of the liquid handling devices with a unique address so that each device may be uniquely addressed by the computer. This is provided by a jumper board 367 which has a plurality of terminals connected to the device 310, and which permits each of the inputs PB0-PB7 of the device 310 to be connected either to ground or to a source of positive potential to thereby define an eight-bit address for each liquid handling device.

The interface between the control switches and the display on the front panel 14 and the microprocessor 300 is provided by the circuitry illustrated in FIG. 21. The interconnections between FIGS. 20 and 21 are indicated by like designated leads. The interface includes a keyboard display controller 370 which is connected to the various keyswitches on the front panel 14 via a plurality of leads 372. The inputs 372 are given row and column designations corresponding to the rows and columns of the keyswitches to which they are connected. Each of the keyswitches contains a pair of contacts that connects one of the row inputs with one of the column inputs when the keyswitch is depressed. Thus, for example, if the keyswitch in the first row of the third column (the keyswitch designated by the numeral 3 in FIG. 1) were depressed, the lead designated Column 3 would be connected to the lead designated Row 1 to indicate to the keyboard display controller 370 that the numeral 3 had been entered.

The keyboard display controller has two sets of outputs, one set being designated as DB0 through DB7 and another set being designated as B0 through B3 and A0 through A3. The set designated as DB0 through DB7 is connected to the data bus and communicates with the microprocessor control board 300 to process the data entered via the keyswitches on the front panel 14. The other set of outputs designated as B0 through B3 and A0 through A1 are connected to a character generator chip 374, which may be a type MSL 9665 character generator chip manufactured by OKI Semiconductor. The character generator chip 374 serves to select the appropriate segment of the display 34 for illumination in accordance with the data present on lines B0 through B3 and A0 through A1. The outputs of the character generator chip 374 are amplified by a pair of drivers 376 and 378, such as, for example, type 6118A drivers manufactured by Sprague, and applied to the appropriate segments of the display 44. In addition, the signals on the outputs A2 and A3 of the keyboard display controller 370 are amplified directly by the driver 378 in order to illuminate a comma and a decimal point, respectively, on the display 34.

The display 34 is preferably a vacuum fluorescent display such as, for example, a type FG169B2. The display 34 utilized in the present embodiment includes sixteen 14-segment displays each capable of displaying all capital letters and numerals, as well as a decimal point and a comma adjacent to each 14-segment display.

In the illustrated embodiment, the sixteen characters of the display 34 are sequentially displayed at a rapid rate so that it appears to the human eye that all characters are simultaneously illuminated. However, in order to achieve such sequential display, the information provided to the display 34 must include information defining which of the sixteen individual displays is to be energized, as well as the character that is to be displayed. As previously discussed, the information defining the character to be displayed is applied to the display 34 via the drivers 376 and 378. The data indicating which of the sixteen individual displays is to be energized is provided by a pair of 16-bit character selectors 380 and 382, which may be, for example, type 74LS359 selectors that cooperate with a pair of drivers 384 and 386 to select the one of the sixteen displays to be energized. Basically, the character selectors 380 and 382 serve as decoders to decode the 4-bit signal at the outputs SL0 through SL3 of the keyboard display controller 370 to select the one of the sixteen character displays to be energized.

Each of the leads designated as Row 0 through Row 3 of the leads 372 is energized in sequence, with each of the row designated leads having an assigned time frame in the sequence. This time frame is interpreted by the keyboard display controller 370 to determine which row designated keyswitch had been depressed. The sequencing information is provided by a decoder 388, which may be a type 74LS156 decoder. The decoder 388 receives four bits of information from the outputs designated SL0 through SL2 and $\overline{BD}$ of the keyboard display 370 and decodes this information to energize Row 0 through Row 3 in sequence. Resistors 390 and 392 serve as pull up resistors for the keyboard display controller 370 and the character generator chip 374, respectively.

The sequence of events performed by the microprocessor control circuitry in the liquid handling device according to the present invention is illustrated in FIG. 22 in flow chart form. When power to the device is first applied, a determination is first made to determine whether a power failure had occurred during a previous operating sequence. If such a power failure had occurred, control would be returned to the point in the porgram where power was lost so that the sequence could be completed. If no power failure had occurred, the step motors would be initialized, and the Z-drive motor would be driven to its upper limits. The program then terminates until the start command is entered.

Upon entry of the start command, the X- and Y-drive motors are driven to their limit or home positions in order to provide a home position reference for further movement. The entered pattern is then read, as are any operation mode and other parameters that may have been entered. The X- and Y- drive motors then move the head to the first tube in the sequence. The next instruction is then read, as are the positions of any switches in order to determine whether any motor should be activated to move the head to an advance position. If movement is required, the head is advanced to the next tube, to the next rack or to the drain, as required. The loop then continues until the necessary advance is completed.

Once the motors have been advanced to the proper position, the pattern selection is read to determine whether the fraction collector or sampling mode has been selected. If the fraction selection mode has been selected, the time over each tube or the number of drops selected, as appropriate is counted. After the counting or timing has been completed, the next instruction is fetched and the sequence is repeated until the complete pattern has been completed.

If the sample mode had been selected, it must first be determined whether or not the Z-drive is active. If so, the Z-drive is moved down to its limit, the preset time over the test tube is counted, and the Z-drive is then moved up again. The instructions are again read, and if necessary, the head is moved to the next test tube. This sequence is continued until the pattern is completed. If the Z-drive were not active, and a pattern loop instruction had been entered, the pattern loop would be followed. If no pattern had been entered, the next instruction, if any, would be read.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. Liquid handling apparatus comprising a table member; rack means supported on said table member for supporting a plurality of receptacles arrayed in predetermined positions above said table member; a subframe having a first portion mounted beneath said table member for rectilinear movement in a horizontal X direction; an X-drive motor supported in a fixed position relative to said table member; X-drive means interconnecting said X-drive motor and said subframe; said subframe including an upstanding portion extending above said table member and a horizontal portion overlying the table member; a Y-drive motor mounted on the first subframe portion; a carriage mounted on said subframe horizontal portion for rectilinear movement in a transverse, horizontal Y direction; Y-drive means interconnecting said Y-drive motor and said carriage; a gantry detachably supported on said carriage; a holder device mounted on said gantry for rectilinear movement in a vertical Z direction; a Z-drive motor mounted on said gantry; Z-drive means coupled between said holder drive and said Z-drive motor, said gantry, holder device, Z-drive motor and Z-drive means being detachable from said carriage as a unit; and control means for selectively energizing said drive motors for moving said carriage into positions corresponding to said receptacle positions and for moving said holder device vertically with respect to said receptacles said X-, Y- and Z-drive motors cooperating with said X-, Y- and Z-drive means and with said control means for selectively moving said holder device in three mutually perpendicular directions.

2. Liquid handling apparatus as claimed in claim 1, further comprising conductor means including a releasable electrical connector releasably interconnecting said Z-drive motor and said control means.

3. Liquid handling apparatus as claimed in claim 1 wherein said X-, Y- and Z-drive means each include a toothed drive sprocket on the corresponding motor, and a drive belt including regularly spaced index means engaged with the sprocket.

4. Liquid handling apparatus as claimed in claim 1, further comprising X-detector means for sensing an X home position of said subframe; Y-detector means for sensing a Y home position of said carriage; and Z-detector means for sensing a Z home position of said device holder; and X-, Y- and Z-detector means being connected to said control means.

5. Liquid handling apparatus as recited in claim 4 wherein said control means includes means for receiving input data, said control means being responsive to the input data for energizing said X-, Y- and Z-drive motors in a predetermined sequence.

6. Liquid handling apparatus as recited in claim 5 wherein said control means is responsive to said X-detector means, said Y-detector means and said Z-detector means for energizing said X-, Y- and Z-drive motors to bring said subframe, said carriage and said device holder to the X, Y and Z home positions, respectively, prior to energizing said X-, Y- and Z-drive motors in the predetermined sequence.

7. Liquid handling apparatus as recited in claim 6 wherein said gantry is detachably mounted on said structure, and said control means is responsive to only said X-detector means and said Y-detector means to bring said subframe and said carriage to the X and Y home positions, respectively, prior to energizing only said X- and Y-drive motors when said gantry is detached.

8. Liquid handling device as recited in claim 6 wherein said X-, Y- and Z-drive motors are stepping motors and wherein said control means includes means for providing a series of sequential pulses to said drive motors, each pulse being operative to advance one of said drive motors by one step.

9. Liquid handling apparatus as recited in claim 8 wherein said control means includes means responsive to the input data to provide each of said drive motors with a predetermined number of pulses in a predetermined sequence to advance said motors a predetermined amount in a predetermined sequence.

10. Liquid handling apparatus as claimed in claim 1, said subframe horizontal portion comprising an extrusion of uniform cross section, and said carriage having a plurality of carriage guide rollers engageable with said extrusion.

11. Liquid handling apparatus as claimed in claim 10, at least one of said carriage guide rollers being adjustably mounted.

12. Liquid handling apparatus as claimed in claim 1, further comprising a pair of circular cross section, spaced apart, parallel guides supported beneath said table member, said subframe having a first and a second set of three subframe guide rollers engaging one said guide at substantially equally angularly spaced positions about the periphery of said one guide; said first and second sets being longitudinally spaced along said one guide, and said subframe having a third set of two subframe guide rollers engaging the other said guide at diametrically opposed sides thereof.

13. Liquid handling apparatus as claimed in claim 1, said rack means including a plate member mounted on the table, first key means permitting said plate member to fit on said table in only one predetermined position; at least one rack mounted on said plate member; and second key means permitting said rack to fit on said plate member in only one predetermined orientation.

14. Liquid handling apparatus as claimed in claim 1 further including means for receiving information from an external device and means responsive to the information received for rendering said control means operative to advance said holder device from one receptable to another upon the receipt of an advancing signal.

15. Liquid handling apparatus as claimed in claim 14 wherein said liquid handling apparatus includes a dispensing tube mounted on said holder device, and is operable in a dispensing mode of operation, and wherein said information responsive means is responsive to information received from a dispenser for controlling the dispensing time of the liquid handling device.

16. Liquid handling apparatus as claimed in claim 14 wherein said information responsive means includes means for delaying the advancement of said holder device by a predetermined time interval following the receipt of said advancing signal, said liquid handling system further including means for manually entering data representative of said predetermined interval.

17. Liquid handling apparatus as claimed in claim 1 wherein said liquid handling apparatus is operable in a sampler mode of operation and includes means including a tube mounted on said holder device for transferring liquid samples from a sample source to a test point, and wherein said liquid handling apparatus includes means for inserting an air bubble after each sample, wherein said bubble inserting apparatus includes means including a keyboard for manually entering data representative of the time said air bubble is inserted.

18. Liquid handling apparatus as claimed in claim 1 wherein said control means is operative selectively to operate said liquid handling apparatus in a fraction collector mode of operation, a diluter mode of operation, a dispenser mode of operation and a sampler mode of operation, wherein said control means includes a microprocessor and a manually operable keyboard for entering data representative of the mode of operation selected.

19. In a liquid handling apparatus such as a fraction collector, sampler or the like, the combination comprising:

a rigid table;
a pair of circular or cross-section guide members supported by said table beneath said table, said guide members being spaced apart and parallel to one another and to said table;
a subframe;
a first group of three subframe guide rollers mounted on said subframe and rollingly engaging one of said guide members at substantially equally angularly spaced locations around the periphery of said one guide member;
a second group of three subframe guide rollers mounted on said subframe and rollingly engaging said one guide member at substantially equally angularly spaced locations around the periphery of said one guide member;
said first and second groups being axially spaced from one another along the guide member;
a third group of two opposing subframe guide rollers mounted on said subframe and rollingly engaging the other of said guide member;
members at substantially diametrically opposed locations on said other guide subframe drive means for moving said subframe along said guide members; and
said subframe including a structure extending above said table.

20. The combination of claim 19, said subframe structure including an upwardly extending mast portion and a horizontally extending beam portion overlying said table.

21. The combination of claim 20, said beam portion extending in a direction transverse to said guide members; a carriage supported by said beam portion for movement along said beam portion; and carriage drive means for moving said carriage along said beam portion.

22. The combination of claim 21, said carriage including releasable attachment means.

23. The combination of claim 22, and a device holder secured to said carriage by said attachment means.

24. The combination of claim 22, further comprising a vertically extending gantry secured to said carriage by said attachment means; said gantry including a vertically movable device holder; and gantry drive means for moving said device holder.

25. The combination of claim 21, said beam comprising an extrusion of uniform cross section.

26. The combination of claim 25, said carriage having a plurality of carriage guide rollers engageable with said extrusion.

27. The combination of claim 26, wherein said extrusion has a pair of upper and a pair of lower tracks integrally formed in the interior thereof, and wherein some of said guide rollers engage said upper track and some of said guide rollers engage said lower track.

28. The combination of claim 27 wherein at least some of said guide rollers are adjustably mounted.

29. The combination of claim 21 including control means for controlling the operation of said subframe drive means and said carriage drive means, and data input means for receiving control data defining the operating sequence of said drive means, said data input means including electrical input means for receiving electrical signals representative of said data.

30. The combination of claim 29, said electrical input means including a parallel input and a serial input.

31. The combination of claim 30 including an electrical connector.

32. The combination of claim 30 wherein said control means includes means for communicating with an external computer via said parallel input and said serial input.

33. The combination of claim 29 wherein said control means includes a microprocessor.

* * * * *